United States Patent
Kocherry et al.

(10) Patent No.: US 12,178,927 B2
(45) Date of Patent: Dec. 31, 2024

(54) GASPER KNOB SANITIZATION

(71) Applicant: B/E AEROSPACE, INC., Winston Salem, NC (US)

(72) Inventors: John John Kocherry, Kerala (IN); Santosh Kumar Tripathy, Bangalore (IN)

(73) Assignee: B/E AEROSPACE, INC., Winston Salem, NC (US)

(*) Notice: Subject to any disclaimer, the term of this patent is extended or adjusted under 35 U.S.C. 154(b) by 396 days.

(21) Appl. No.: 17/590,730

(22) Filed: Feb. 1, 2022

(65) Prior Publication Data
US 2022/0241442 A1 Aug. 4, 2022

(30) Foreign Application Priority Data
Feb. 2, 2021 (IN) .............................. 202141004518

(51) Int. Cl.
*A61L 2/10* (2006.01)
*B64D 11/00* (2006.01)
*B64D 13/06* (2006.01)

(52) U.S. Cl.
CPC ................ *A61L 2/10* (2013.01); *B64D 11/00* (2013.01); *B64D 13/06* (2013.01);
(Continued)

(58) Field of Classification Search
CPC ....... A61L 2/10; A61L 2202/11; B64D 11/00; B64D 11/0626; B64D 13/06; B64D 13/00;
(Continued)

(56) References Cited

U.S. PATENT DOCUMENTS

| 6,787,782 B1 | 9/2004 | Krosney et al. | |
| 11,572,171 B2 * | 2/2023 | Quatmann | B60Q 3/47 |

(Continued)

FOREIGN PATENT DOCUMENTS

| CN | 209143418 U | 7/2019 |
| JP | 2011143994 | 7/2011 |

(Continued)

OTHER PUBLICATIONS

Extended European Search Report for European Patent Application No. EP22154820.9, dated Jun. 8, 2022.
(Continued)

*Primary Examiner* — Kiet T Nguyen
(74) *Attorney, Agent, or Firm* — SNELL & WILMER L.L.P.

(57) ABSTRACT

An air gasper knob system for an overhead Passenger Service Unit (PSU) includes an annular gasper knob of a UV transparent material. The annular gasper knob defines an air passage therethrough, and extends about the air passage from a first annular end face to a second annular end face. The system also includes a UV illuminator mounted to the gasper knob, oriented to transmit UV illumination through the UV transparent material to sanitize exterior surfaces of the gasper knob. A method of sanitizing an air gasper knob comprises illuminating a gasper knob in an overhead PSU using UV illumination to destroy infectious agents on surfaces of the gasper knob.

10 Claims, 3 Drawing Sheets

(52) U.S. Cl.
CPC ... *A61L 2202/11* (2013.01); *B64D 2011/0053* (2013.01); *B64D 2013/0603* (2013.01)

(58) Field of Classification Search
CPC .... B64D 2011/0053; B64D 2013/0603; B64D 2013/003; B64F 5/30
USPC .................................................. 250/455.11
See application file for complete search history.

(56) References Cited

U.S. PATENT DOCUMENTS

| | | |
|---|---|---|
| 2015/0090839 A1 | 4/2015 | Freund et al. |
| 2018/0361002 A1 | 12/2018 | Mastrocola |

FOREIGN PATENT DOCUMENTS

| | | |
|---|---|---|
| KP | 2016015082 | 2/2016 |
| WO | WO-2017204774 A1 | 11/2017 |
| WO | WO-2020146138 A1 | 7/2020 |

OTHER PUBLICATIONS

European Patent Office, European Office Action dated Jan. 18, 2024 in Application No. 22154820.9.

\* cited by examiner

GASPER KNOB SANITIZATION

RELATED APPLICATIONS

This application claims priority to and the benefit of Indian Patent Application No. IN202141004518, filed Feb. 2, 2021, which is incorporated herein by reference in its entirety.

BACKGROUND

1. Field

This invention relates to sanitization of aircraft interiors, and in particular sanitization of gasper knobs in aircraft interiors

2. Description of Related Art

The pandemic of 2020 has changed procedures and protocols for travel. While travel continues, and vaccines can be deployed to eventually control pandemics, it is clear that changes must be made to help prevent the spread of infection diseases. Aircraft interiors are the subject of scrutiny for how to reduce spread of contagions during flight from passenger to passenger, as well as between flights from one flight of passengers to the subsequent flight of passengers. Various schemes have been suggested and/or implemented, including spraying the passenger cabin with disinfectant sprays between flights.

While the current and traditional techniques have been considered sufficient for their intended purposes, there is an ongoing need for improvements to sanitizing aircraft interiors. This disclosure provides solutions to this need.

SUMMARY

An air gasper knob system for an overhead Passenger Service Unit (PSU) includes an annular gasper knob of a UV transparent material. The annular gasper knob defines an air passage therethrough, and extends about the air passage from a first annular end face to a second annular end face. The system also includes a UV illuminator mounted to the gasper knob, oriented to transmit UV illumination through the UV transparent material to sanitize exterior surfaces of the gasper knob.

The UV illuminator can be embedded in the gasper knob and can include a light emitting diode (LED) configured to emit UV illumination. The UV illuminator can be a strip of LEDs configured to emit UV illumination, and the strip of LEDs can be annular and embedded in the gasper knob proximate to the first annular end face of the gasper knob. The strip of LEDs can be embedded in the gasper knob so that the LEDs are oriented to illuminate toward the second annular end face of the gasper knob.

The system can also include a valve assembly configured to open and close a flow of air by turning the gasper knob about an axis of rotation. The first annular end face of the gasper knob can be at an inlet end of the gasper knob mounted to the valve assembly, and the second annular end face of the gasper knob can be at an outlet end of the gasper knob extending away from the nozzle assembly. The nozzle assembly can include a central cone configured to engage and disengage a rim in the valve assembly by turning of the gasper knob to control air flow through the gasper knob from a pressurized air source in fluid communication with the nozzle assembly.

The system can further include at least one reading light and/or at least one flight attendant call button mounted in a PSU panel with the nozzle assembly. The at least one reading light and/or at least one flight attendant call button can be electrically connected to a source of electrical power, and the LEDs can be electrically connected to the source of electrical power. The gasper knob can be one of a plurality of gasper knobs each having a respective illuminator electrically connected to the source of electrical power.

A method of sanitizing an air gasper knob comprises illuminating a gasper knob in an overhead PSU using UV illumination to destroy infectious agents on surfaces of the gasper knob. Illuminating the gasper knob can include illuminating all exposed surfaces of the gasper knob. Illuminating the gasper knob can also include using a UV illuminator embedded in the gasper knob.

The method can include powering the illuminator with a supply of electrical power within the PSU. The method can also include illuminating the UV illuminator after passengers have disembarked the aircraft cabin. The method can further include deactivating the illuminator prior to passengers boarding the aircraft cabin.

These and other features of the systems and methods of the subject disclosure will become more readily apparent to those skilled in the art from the following detailed description taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, embodiments thereof will be described in detail herein below with reference to certain figures, wherein.

DETAILED DESCRIPTION

Figure 1:
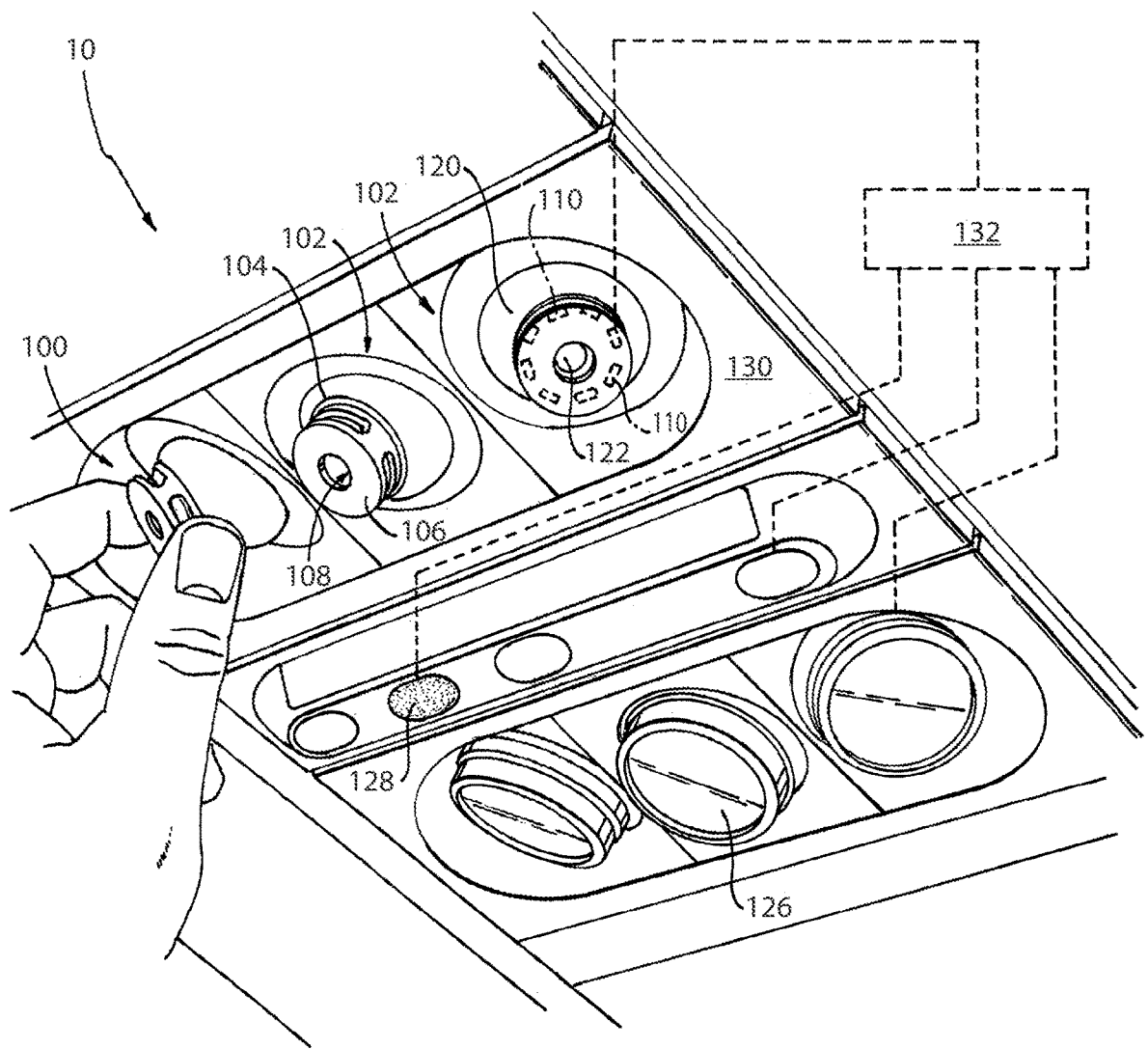
FIG. 1 is a schematic perspective view of an embodiment of a passenger service unit constructed in accordance with the present disclosure, showing a gasper knob.
Figure 2:
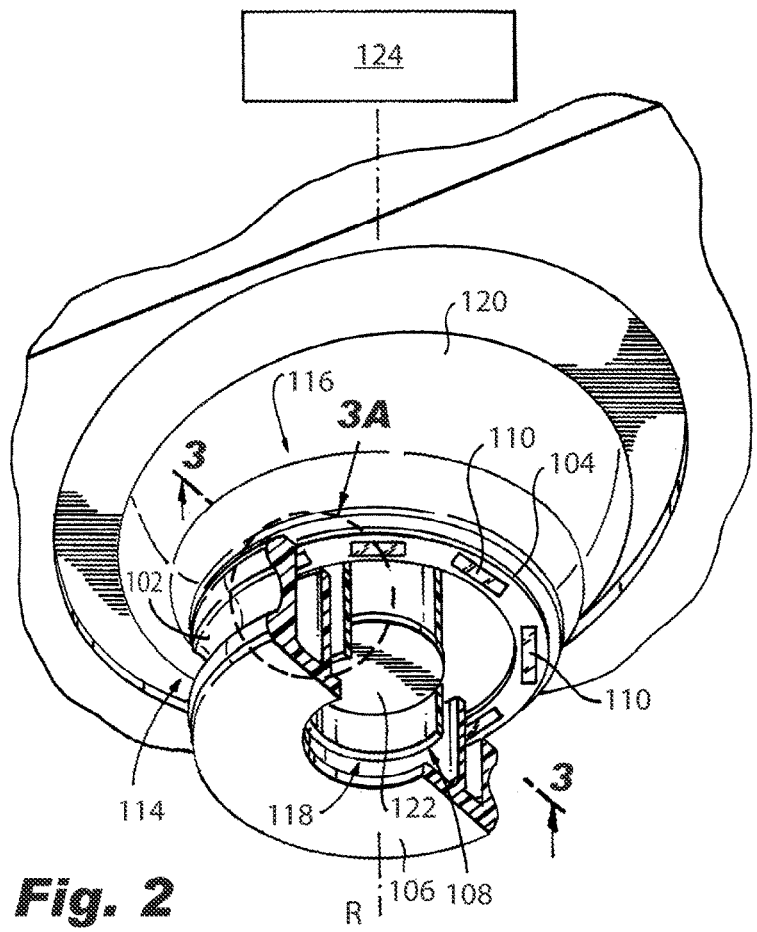
FIG. 2 is a schematic perspective cross-sectional view of the gasper knob of FIG. 1.
Figure 3A:
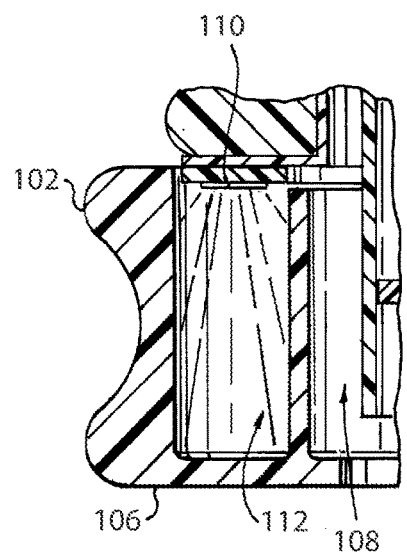
FIG. 3A is a schematic cross sectional view of the gasper knob showing an illuminator.
Figure 3:
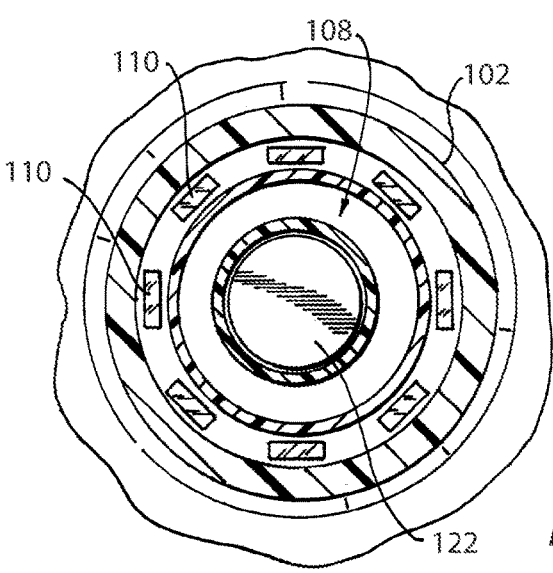
FIG. 3 is a schematic cross sectional view of the gasper knob of FIGS. 1-2, looking upstream.
Figure 4:
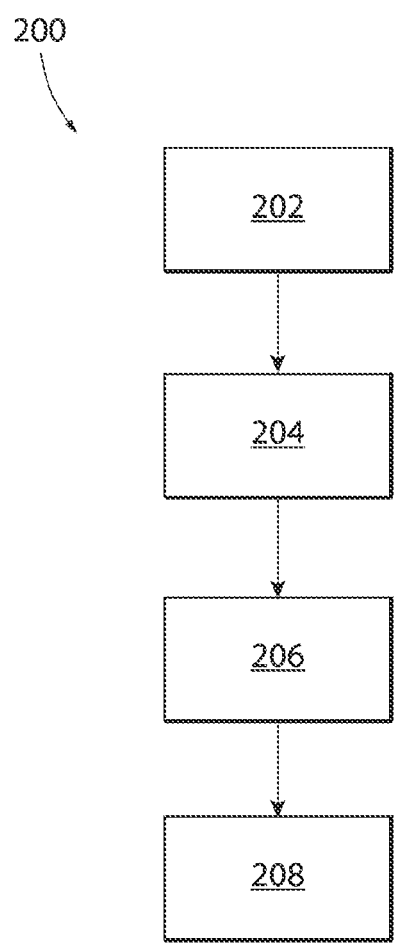
FIG. 4 is schematic box diagram of a method.

Reference will now be made to the drawings wherein like reference numerals identify similar structural features or aspects of the subject disclosure. For purposes of explanation and illustration, and not limitation, a partial view of an embodiment of a system in accordance with the disclosure is shown in FIG. 1 and is designated generally by reference character 100. Other embodiments of systems in accordance with the disclosure, or aspects thereof, are provided in FIGS. 2-4, as will be described. The systems and methods described herein can be used to sanitize gasper knobs.

An air gasper knob system 100 for an overhead Passenger Service Unit (PSU) 10 can include at least one annular gasper knob 102 of a UV transparent material, the knob 102 having a first annular end face 104 and a second annular end face 106. The annular gasper knob 102 can define an air passage 108, and can extend about the air passage 106, for example from the first annular end face 104 to the second annular end face 106.

The system 100 can also include a UV illuminator 110 mounted to the gasper knob 102. For example, the UV illuminator 110 can include a light emitting diode (LED) configured to emit UV illumination 112 through the UV transparent material, or can include a strip of LEDs. The UV illuminator 110 can be oriented to sanitize exterior surfaces of the gasper knob 102. For example, the UV illuminator 110 can be embedded (e.g. via additive manufacturing) in the gasper knob 102 and if the UV illuminator is a strip of LEDS, the strip can be annular and embedded in the gasper knob 102 proximate to the first annular end face 104 of the gasper knob 102. In this configuration, the strip of LEDs can be embedded in the gasper knob so that the LEDs are oriented to illuminate toward the second annular end face 106 of the gasper knob 102. Typically when sanitizing surfaces with UV illumination, surfaces of small components, such as gasper knobs 102, might escape the UV rays line of sight and might not get effectively sanitized if UV illumination is applied to the cabin indiscriminately. By embedding the UV illuminator directly in the gasper knob 102, such as described herein, effective sanitization of the gasper knob 102 can be achieved.

The system 100 can also include a valve assembly 114 configured to open and close a flow of air by turning (e.g. twisting) the gasper knob about an axis of rotation R. The first annular end face 104 can be at an inlet end 116 of the gasper knob 102 mounted to the valve assembly 114, and the second annular end face 106 can be at an outlet end 118 of the gasper knob 102, extending away from the nozzle assembly 114. In embodiments, the nozzle assembly 114 can include a central cone 120 configured to engage and disengage a rim 122 in the valve assembly 114. For example, the air flow through the gasper knob 102 can be controlled by turning the gasper knob 102, where in the open position, air from a pressurized air source 124 can be fluid communication with the nozzle assembly 114, and in the closed position, airflow from the pressurized source 124 can be restricted.

The system 100 can further include, for example in the PSU 10 at least one reading light 126 and/or at least one flight attendant call button 128 mounted in a PSU panel 130 with the nozzle assembly 114. The reading light(s) 126 and call button(s) 128 can be electrically connected to a source of electrical power 132, and the UV illuminator(s) 110 can be electrically connected to the same source of electrical power 132. If the system 100 includes a plurality of gasper knobs 102, each knob 102 can include its own UV illuminator 110, and each UV illuminator 110 can also be electrically connected to the source of electrical power 132.

A method 200 of sanitizing an air gasper knob (e.g. knob 102) in a PSU 10 can include, at box 202, illuminating a gasper knob 102 in an overhead PSU 110 using UV illumination (e.g. using illuminator 110) to destroy infectious agents (e.g. bacteria and/or viruses) on surfaces of the gasper knob 102. Illuminating 202 the gasper knob can include illuminating all exposed surfaces of the gasper knob 102, for example all surfaces in which a passenger seated below the PSU 10 may interact with during the flight. This can be accomplished using embedded illuminators that transmit illumination through the gasper knob itself. During flight, a passenger typically adjusts the air flow rate through the gasper knob by adjusting it manually, as described above. Micro-organisms and other infectious agents present on the hands of a passenger may then transfer from the hand of the passenger to the external surface of the gasper knob and then to the air outlet. This can provide a pathway for microorganisms to spread inside the cabin through air coming from the gasper outlet, in addition to a passenger in the next flight coming into contact with any microorganisms left behind.

The method 200 can include powering the illuminator 110 with a supply of electrical power within the PSU 10, for example using source of electrical power 132, as shown at box 204. At box 206, the method 200 can also include illuminating the UV illuminator 110 after passengers have disembarked the aircraft cabin. At box 208, the method 200 can further include deactivating the illuminator 110 prior to passengers boarding the aircraft cabin, for example so passengers are not exposed to UV radiation from the UV illuminator 110. The UV illuminators 110 can be connected so that they can be activated and deactivated by a non-passenger user (e.g. flight staff) using a single switch.

These and other features of the systems and methods of the subject disclosure will become more readily apparent to those skilled in the art from the following detailed description taken in conjunction with the drawings. The methods and systems of the present disclosure, as described above and shown in the drawings, provide for more efficient and effective sanitization of small aircraft components, such as gasper knobs and other equipment within a passenger service unit. While the apparatus and methods of the subject disclosure have been shown and described, those skilled in the art will readily appreciate that changes and/or modifications may be made thereto without departing from the scope of the subject disclosure.

What is claimed is:

1. An air gasper knob system for an overhead Passenger Service Unit (PSU), the system comprising:
    an annular gasper knob of a UV transparent material, wherein the annular gasper knob defines an air passage therethrough, and where the annular gasper knob extends about the air passage from a first annular end face to a second annular end face; and
    a UV illuminator mounted to the gasper knob, oriented to transmit UV illumination through the UV transparent material to sanitize exterior surfaces of the gasper knob.

2. The system as recited in claim 1, wherein the UV illuminator is embedded in the gasper knob.

3. The system as recited in claim 1, wherein the UV illuminator includes a light emitting diode (LED) configured to emit UV illumination.

4. The system as recited in claim 1, wherein the UV illuminator includes a strip of LEDs configured to emit UV illumination.

5. The system as recited in claim 4, wherein the strip of LEDs is annular and is embedded in the gasper knob proximate to the first annular end face of the gasper knob.

6. The system as recited in claim 5, wherein the strip of LEDs is embedded in the gasper knob with the LEDs oriented to illuminate toward the second annular end face of the gasper knob.

7. The system as recited in claim 6, further comprising a valve assembly configured to open and close a flow of air by turning the gasper knob about an axis of rotation, wherein the first annular end face of the gasper knob is at an inlet end of the gasper knob mounted to the valve assembly, and wherein the second annular end face of the gasper knob is at an outlet end of the gasper knob extending away from a nozzle assembly.

8. The system as recited in claim 7, wherein the nozzle assembly includes a central cone configured to engage and disengage a rim in the valve assembly by turning of the gasper knob to control air flow through the gasper knob from a pressurized air source in fluid communication with the nozzle assembly.

9. The system as recited in claim 8, further comprising at least one reading light and/or at least one flight attendant call button mounted in a PSU panel with the nozzle assembly, wherein the at least one reading light and/or at least one flight attendant call button are electrically connected to a source of electrical power, and wherein the LEDs are electrically connected to the source of electrical power.

10. The system as recited in claim 9, wherein the gasper knob is one of a plurality of gasper knobs each having a respective illuminator electrically connected to the source of electrical power.

* * * * *